(12) United States Patent
Lang

(10) Patent No.: US 11,144,740 B2
(45) Date of Patent: Oct. 12, 2021

(54) READER FOR MEDICAL IMPLANTS

(71) Applicant: Shilei Lang, Hong Kong (HK)

(72) Inventor: Shilei Lang, Hong Kong (HK)

(73) Assignee: SHENZHEN DANSHA TECHNOLOGY CO., LTD., Guangdong (CN)

(*) Notice: Subject to any disclaimer, the term of this patent is extended or adjusted under 35 U.S.C. 154(b) by 266 days.

(21) Appl. No.: 16/244,078

(22) Filed: Jan. 9, 2019

(65) Prior Publication Data
US 2019/0147204 A1 May 16, 2019

(51) Int. Cl.
*G06K 7/10* (2006.01)
*H03F 3/24* (2006.01)
(Continued)

(52) U.S. Cl.
CPC ..... *G06K 7/10316* (2013.01); *G06K 7/10009* (2013.01); *H03F 1/56* (2013.01); *H03F 3/245* (2013.01); *H03F 3/45183* (2013.01); *H03F 3/45475* (2013.01); *H04B 1/0458* (2013.01); *H04B 1/0475* (2013.01); *A61F 2/02* (2013.01); *A61F 2250/0001* (2013.01); *A61F 2250/0085* (2013.01); *H03F 2200/171* (2013.01); *H03F 2200/294* (2013.01); *H03F 2200/387* (2013.01);
(Continued)

(58) Field of Classification Search
CPC .. G06K 7/10316; G06K 7/10009; H03F 1/56; H03F 3/245; H03F 3/45183; H03F 3/45475; H03F 2200/171; H03F 2200/294; H03F 2200/387; H03F 2200/451; H04B 1/0458; H04B 2001/0408; H04B 2001/045; H04B 1/0475; A61F 2/02; A61F 2250/0001; A61F 2250/0085
USPC ............................ 455/114.2, 41.1, 41.2, 41.3
See application file for complete search history.

(56) References Cited

U.S. PATENT DOCUMENTS

2002/0032471 A1* 3/2002 Loftin ................ A61N 1/37211
607/61
2006/0232408 A1* 10/2006 Nycz ...................... A61B 90/90
340/572.1
(Continued)

FOREIGN PATENT DOCUMENTS

| CN | 107809220 A | 3/2018 |
| JP | H29-147681 A | 8/2017 |
| WO | 2013/006954 A1 | 1/2013 |

*Primary Examiner* — Ankur Jain

(57) ABSTRACT

A reader for medical implants includes an antenna and a transceiver chip connected with the antenna. The transceiver chip includes a power amplifier and a resistor. The power amplifier is connected with a reference voltage through the resistor and configured to produce a first communication signal with high frequency and transmit the first communication signal to the medical implants through the antenna. The medical implant receives the first communication signal and produces a second communication signal according to variation of parameters of the medical implant. The antenna is configured to receive the second communication signal. The power amplifier is further configured to vary a DC current which flows through the resistor according to the second communication signal and read signals of the medical implant according to variation of the DC current. The power amplifier is further configured to modulate the second communication signal into a low frequency signal.

18 Claims, 3 Drawing Sheets

(51) Int. Cl.
   *H03F 1/56*    (2006.01)
   *H03F 3/45*    (2006.01)
   *H04B 1/04*    (2006.01)
   *A61F 2/02*    (2006.01)

(52) U.S. Cl.
   CPC .. *H03F 2200/451* (2013.01); *H04B 2001/045* (2013.01); *H04B 2001/0408* (2013.01)

(56) References Cited

U.S. PATENT DOCUMENTS

| | | | |
|---|---|---|---|
| 2011/0022411 A1* | 1/2011 | Hjelm | H04L 67/24 |
| | | | 705/2 |
| 2012/0050015 A1 | 3/2012 | Low et al. | |
| 2013/0169416 A1 | 7/2013 | Rezayee | |
| 2016/0268980 A1 | 9/2016 | Seong et al. | |
| 2017/0180010 A1* | 6/2017 | Michel | G06K 7/10009 |
| 2017/0237469 A1* | 8/2017 | Taghivand | H04B 5/0037 |
| | | | 455/41.1 |

* cited by examiner

READER FOR MEDICAL IMPLANTS

FIELD OF THE PATENT APPLICATION

The present patent application generally relates to medical electronics and more specifically to a reader for medical implants.

BACKGROUND

Realizing the interconnection between a human body and electronic devices is of great importance to future medical treatment and research. RFID readers with a small size and high efficiency are especially needed to acquire neural signals of a human body. Such readers can provide power for RFID tags in medical implants of a human body and communicate with the RFID tags so as to reduce damage produced by a surgery for changing a battery and maintain stable communication at the same time. A conventional RFID system often has carrier leakage from its transmission port to its receiving port, so that the frontend circuit of the receiving port is saturated and the redundant phase noise of the transmission port may reduce the sensitivity of the receiving port. In some systems, the RFIDs are designed in a way that power supply and communication are realized through separate coils. Such RFIDs occupy relatively large space, and therefore are not suitable for medical implants of a human body. There are also some single-coil systems which often require a circulator and an isolator to be disposed outside the chip, and therefore also occupy relatively large space.

SUMMARY

The present patent application is directed to a reader for medical implants configured to read signals of a medical implant. In one aspect, the reader for medical implants includes an impedance matching network; an antenna; and a transceiver chip. The transceiver chip is electrically connected with the antenna through the impedance matching network. The transceiver chip is configured to produce a first communication signal with high frequency and transmit the first communication signal to the medical implant through the impedance matching network and the antenna. The medical implant receives the first communication signal and produces a second communication signal according to variation of parameters of the medical implant. The antenna is configured to receive the second communication signal and transmit the second communication signal to the transceiver chip through the impedance matching network. The transceiver chip is further configured to read signals of the medical implant according to the second communication signal. The transceiver chip is further configured to modulate the second communication signal into a low frequency signal, so that the first communication signal can be separated from the second communication signal in frequency and interference between the first communication signal and the second communication signal can be avoided. The transceiver chip includes a power amplifier, a resistor and a signal processing module. The power amplifier includes a first input port, a second input port, a first output port, a second output port, a voltage port and a signal output port. The first input port and the second input port are configured to receive a driving voltage signal. The power amplifier is configured to produce the first communication signal with high frequency according to the driving voltage signal and transmit the first communication signal to the impedance matching network through the first output port and the second output port. The voltage port is electrically connected with a reference voltage through the resistor. The power amplifier is further configured to vary a DC current which flows through the resistor according to the second communication signal and read signals of the medical implant according to variation of the DC current. The signal processing module is configured to filter interference signals from the DC current, produce a filtered signal and transmit the filtered signal to an external electronic device through the signal output port. The power amplifier further includes a symmetric inductor structure, a first amplifying module and a second amplifying module. The symmetric inductor structure is electrically connected with the voltage port. The first amplifying module includes a first electronic switch and a second electronic switch which are connected in series with each other. The first electronic switch and the second electronic switch are N-type Metal-Oxide Semiconductor Field Effect Transistors, each including a gate electrode, a drain electrode and a source electrode. The gate electrode of the first electronic switch is electrically connected with the reference voltage, the drain electrode of the first electronic switch being electrically connected with the symmetric inductor structure and the first output port, the source electrode of the first electronic switch being electrically connected with the drain electrode of the second electronic switch. The gate electrode of the second electronic switch is electrically connected with the first input port and the source electrode of the second electronic switch is connected to the ground. The structure of the second amplifying module is the same as the structure of the first amplifying module while the second amplifying module includes a third electronic switch and a fourth electronic switch which are connected in series with each other. The third electronic switch and the fourth electronic switch are N-type Metal-Oxide Semiconductor Field Effect Transistors, each including a gate electrode, a drain electrode and a source electrode. The gate electrode of the third electronic switch is electrically connected with the reference voltage, the drain electrode of the third electronic switch being electrically connected with the symmetric inductor structure and the second output port, the source electrode of the third electronic switch being electrically connected with the drain electrode of the fourth electronic switch. The gate electrode of the fourth electronic switch is electrically connected with the second input port and the source electrode of the fourth electronic switch is connected to the ground.

The symmetric inductor structure may have high quality factors and may include a first inductor, a second inductor and a third inductor. Two ports of the first inductor may be electrically connected with the second inductor and the drain electrode of the first electronic switch respectively. Two ports of the second inductor may be electrically connected with the first inductor and the drain electrode of the third electronic switch respectively. One port of the third inductor may be electrically connected with an intersection of the first inductor and the second inductor while the other port of the third inductor may be electrically connected with the voltage port.

In another aspect, the present patent application provides a reader for medical implants configured to read signals of a medical implant. The reader for medical implants includes an antenna; and a transceiver chip connected with the antenna. The transceiver chip includes a power amplifier and a resistor. The power amplifier is electrically connected with a reference voltage through the resistor. The power amplifier is configured to produce a first communication signal with high frequency and transmit the first communication signal to the medical implant through the antenna. The medical implant receives the first communication signal and produces a second communication signal according to variation of parameters of the medical implant. The power amplifier is configured to receive the second communication signal through the antenna so as to vary a DC current which flows through the resistor and read signals of the medical implant according to variation of the DC current. The power amplifier is further configured to modulate the second communication signal into a low frequency signal, so that the first communication signal can be separated from the second communication signal in frequency and interference between the first communication signal and the second communication signal can be avoided.

The power amplifier may include a first input port, a second input port, a first output port, a second output port, a voltage port and a signal output port. The first input port and the second input port may be configured to receive a driving voltage signal. The power amplifier may be configured to produce the first communication signal with high frequency according to the driving voltage signal. The first output port and the second output port may be configured to output the first communication signal. The voltage port may be electrically connected with the reference voltage through the resistor. The power amplifier may be configured to vary the DC current which flows through the resistor according to the second communication signal.

The signal output port may be configured to transmit the DC current to an external electronic device.

The power amplifier may further include a symmetric inductor structure, a first amplifying module and a second amplifying module. The symmetric inductor structure may be electrically connected with the reference voltage through the resistor. The first amplifying module may be electrically connected with the symmetric inductor structure and the first output port and configured to increase the maximum voltage of the first output port. The second amplifying module may be electrically connected with the symmetric inductor structure and the second output port and configured to increase the maximum voltage of the second output port.

The symmetric inductor structure may have high quality factors and include a first inductor, a second inductor and a third inductor. The first inductor may be electrically connected with the second inductor. One port of the third inductor may be electrically connected with an intersection of the first inductor and the second inductor while the other port of the third inductor may be electrically connected with the voltage port.

The first amplifying module may include a first electronic switch and a second electronic switch which are connected in series with each other. The first electronic switch and the second electronic switch may be N-type Metal-Oxide Semiconductor Field Effect Transistors, each including a gate electrode, a drain electrode and a source electrode. The gate electrode of the first electronic switch may be electrically connected with the reference voltage, the drain electrode of the first electronic switch may be electrically connected with the first output port and a port of the first inductor away from the second inductor, the source electrode of the first electronic switch may be electrically connected with the drain electrode of the second electronic switch. The gate electrode of the second electronic switch may be electrically connected with the first input port while the source electrode of the second electronic switch may be connected to the ground. The structure of the second amplifying module may be the same as the structure of the first amplifying module while the second amplifying module may include a third electronic switch and a fourth electronic switch which may be connected in series with each other. The third electronic switch and the fourth electronic switch may be N-type Metal-Oxide Semiconductor Field Effect Transistors, each including a gate electrode, a drain electrode and a source electrode. The gate electrode of the third electronic switch may be electrically connected with the reference voltage, the drain electrode of the third electronic switch may be electrically connected with the second output port and a port of the second inductor away from the first inductor, the source electrode of the third electronic switch may be electrically connected with the drain electrode of the fourth electronic switch; the gate electrode of the fourth electronic switch may be electrically connected with the second input port while the source electrode of the fourth electronic switch may be connected to the ground.

The power amplifier may further include a first capacitor, a second capacitor and a third capacitor. The first capacitor may be connected in parallel with the first inductor and the second inductor, while the first inductor and the second inductor may be connected in series with each other. The second capacitor may be connected in parallel with the first amplifying module. The third capacitor may be connected in parallel with the second amplifying module.

The transceiver chip may further include a signal processing module configured to filter interference signals from the DC current. One port of the signal processing module may be electrically connected with the voltage port while the other port of the signal processing module may be electrically connected with the signal output port.

The reader for medical implants may further include an impedance matching network. The transceiver chip may be electrically connected with the antenna through the impedance matching network. The impedance matching network may be electrically connected with the transceiver chip and configured to optimize transmission efficiency of the first communication signal which may be transmitted by the transceiver chip through impedance matching. The antenna may be electrically connected with the impedance matching network and configured to transmit the first communication signal which may be modulated by the impedance matching network and further configured to transmit the second communication signal to the impedance matching network. The impedance matching network may be further configured to modulate the second communication signal so that receiving efficiency of the second communication signal may be optimized.

In yet another aspect, the present patent application provides a reader for medical implants configured to read signals of a medical implant. The reader for medical implants includes an antenna; and a transceiver chip connected with the antenna. The transceiver chip includes a power amplifier and a resistor. The power amplifier is electrically connected with a reference voltage through the resistor.

The power amplifier may be configured to produce a first communication signal with high frequency and transmit the first communication signal to the medical implant through the antenna. The medical implant may receive the first communication signal and produce a second communication signal according to variation of parameters of the medical implant. The power amplifier may be configured to receive the second communication signal through the antenna so as to vary a DC current which may flow through the resistor and read signals of the medical implant according to variation of the DC current.

The power amplifier may be further configured to modulate the second communication signal into a low frequency signal, so that the first communication signal may be separated from the second communication signal in frequency and interference between the first communication signal and the second communication signal may be avoided.

The power amplifier may include a first input port, a second input port, a first output port, a second output port, a voltage port and a signal output port. The first input port and the second input port may be configured to receive a driving voltage signal. The power amplifier may be configured to produce the first communication signal with high frequency according to the driving voltage signal. The first output port and the second output port may be configured to output the first communication signal. The voltage port may be electrically connected with the reference voltage through the resistor. The power amplifier may be configured to vary the DC current which may flow through the resistor according to the second communication signal. The signal output port may be configured to transmit the DC current to an external electronic device.

The power amplifier may further include a symmetric inductor structure, a first amplifying module and a second amplifying module. The symmetric inductor structure may be electrically connected with the reference voltage through the resistor. The first amplifying module may be electrically connected with the symmetric inductor structure and the first output port and configured to increase the maximum voltage of the first output port. The second amplifying module may be electrically connected with the symmetric inductor structure and the second output port and configured to increase the maximum voltage of the second output port.

The symmetric inductor structure may have high quality factors and may include a first inductor, a second inductor and a third inductor. The first inductor may be electrically connected with the second inductor. One port of the third inductor may be electrically connected with an intersection of the first inductor and the second inductor while the other port of the third inductor may be electrically connected with the voltage port.

The first amplifying module may include a first electronic switch and a second electronic switch which may be connected in series with each other. The first electronic switch and the second electronic switch may be N-type Metal-Oxide Semiconductor Field Effect Transistors, each including a gate electrode, a drain electrode and a source electrode. The gate electrode of the first electronic switch may be electrically connected with the reference voltage, the drain electrode of the first electronic switch may be electrically connected with the first output port and a port of the first inductor away from the second inductor, the source electrode of the first electronic switch may be electrically connected with the drain electrode of the second electronic switch; the gate electrode of the second electronic switch may be electrically connected with the first input port while the source electrode of the second electronic switch may be connected to the ground. The structure of the second amplifying module may be the same as the structure of the first amplifying module while the second amplifying module may include a third electronic switch and a fourth electronic switch which may be connected in series with each other. The third electronic switch and the fourth electronic switch may be N-type Metal-Oxide Semiconductor Field Effect Transistors, each including a gate electrode, a drain electrode and a source electrode. The gate electrode of the third electronic switch may be electrically connected with the reference voltage, the drain electrode of the third electronic switch may be electrically connected with the second output port and a port of the second inductor away from the first inductor, the source electrode of the third electronic switch may be electrically connected with the drain electrode of the fourth electronic switch. The gate electrode of the fourth electronic switch may be electrically connected with the second input port while the source electrode of the fourth electronic switch may be connected to the ground.

The power amplifier may further include a first capacitor, a second capacitor and a third capacitor. The first capacitor may be connected in parallel with the first inductor and the second inductor, while the first inductor and the second inductor may be connected in series with each other. The second capacitor may be connected in parallel with the first amplifying module. The third capacitor may be connected in parallel with the second amplifying module.

The transceiver chip may further include a signal processing module configured to filter interference signals from the DC current. One port of the signal processing module may be electrically connected with the voltage port while the other port of the signal processing module may be electrically connected with the signal output port.

The reader for medical implants may further include an impedance matching network. The transceiver chip may be electrically connected with the antenna through the impedance matching network. The impedance matching network may be electrically connected with the transceiver chip and configured to optimize transmission efficiency of the first communication signal which may be transmitted by the transceiver chip through impedance matching. The antenna may be electrically connected with the impedance matching network and configured to transmit the first communication signal which may be modulated by the impedance matching network and further configured to transmit the second communication signal to the impedance matching network. The impedance matching network may be further configured to modulate the second communication signal so that receiving efficiency of the second communication signal may be optimized.

DETAILED DESCRIPTION

Figure 1:
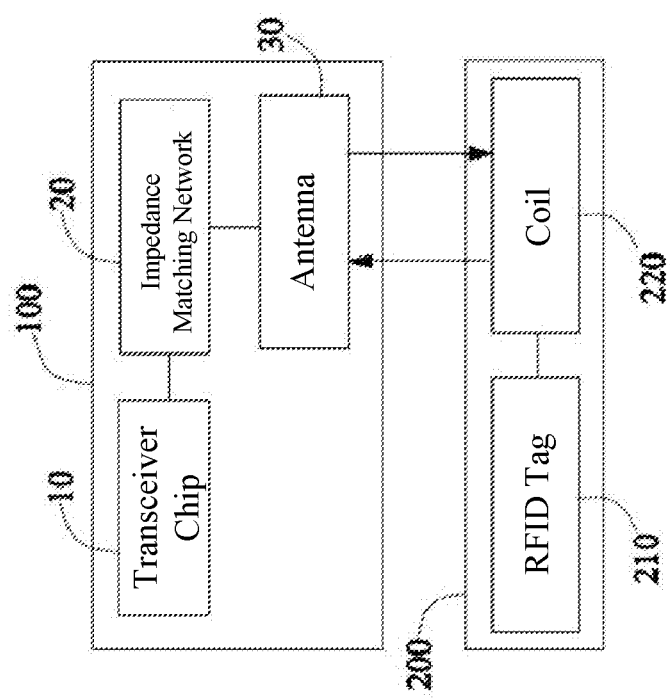
FIG. 1 is a block diagram of a reader for medical implants and a medical implant in accordance with an embodiment of the present patent application.

FIG. 1 is a block diagram of a reader 100 for medical implants and a medical implant 200 in accordance with an embodiment of the present patent application. The medical implant 200 is disposed in a living organism (e.g. a human body). The reader 100 for medical implants is configured to provide a first communication signal with high frequency for the medical implant 200. The medical implant 200 receives the first communication signal and produces a second communication signal according to the variation of parameters of the medical implant 200. The reader 100 for medical implants is further configured to read signals of the medical implant 200 according to the second communication signal.

Referring to FIG. 1, the medical implant 200 includes an RFID (Radio Frequency Identification) tag 210 and a coil 220.

The RFID tag 210 has a unique electronic code and is configured to identify a target object (e.g. a human cerebral neuron). In this embodiment, the RFID tag 210 is a passive tag does not need a power supply so that surgery damages to a living organism resulted from changing a battery can be avoided.

The coil 220 is electrically connected with the RFID tag 210 and configured to receive the first communication signal and transmit the first communication signal to the RFID tag 210. The RFID tag 210 receives the first communication signal and produces the second communication signal according to the variation of parameters of the RFID tag 210. Specifically, when the RFID tag 210 receives the first communication signal, an integrated circuit inside the RFID tag 210 is driven by the electromagnetic waves of the first communication signal and begins to operate. Neurons of a human body have bioelectricity which can vary some parameter (e.g. impedance) of a corresponding RFID tag 210, and therefore some slight variation of neurons of a human body can be sensed by the corresponding RFID tag 210 so as to produce the second communication signal. Multiple sensing chips are integrated in the RFID tag 210 and the multiple sensing chips are individually corresponding to multiple neurons so that each sensing chip can sense the variation of a corresponding neuron. The second communication signal includes not only an ID of the RFID tag 210, but also serial numbers of the multiple sensing chips inside the RFID tag 210 and data sensed by the multiple sensing chips.

The coil 220 is further configured to transmit the second communication signal which is transmitted by the RFID tag 210.

The reader 100 for medical implants includes a transceiver chip 10, an impedance matching network 20 and an antenna 30.

The transceiver chip 10 is configured to produce the first communication signal with high frequency, receive the second communication signal and separate the first communication signal and the second communication signal.

The impedance matching network 20 is electrically connected with the transceiver chip 10 and configured to optimize the transmission efficiency of the first communication signal transmitted by the transceiver chip 10 through impedance matching.

The antenna 30 is electrically connected with the impedance matching network 20 and configured to transmit the first communication signal which is modulated by the impedance matching network 20, receive the second communication signal transmitted by the medical implant 200 and transmit the second communication signal to the impedance matching network 20.

The impedance matching network 20 is further configured to modulate the second communication signal, so that the receiving efficiency of the second communication signal is optimized.

Figure 2:
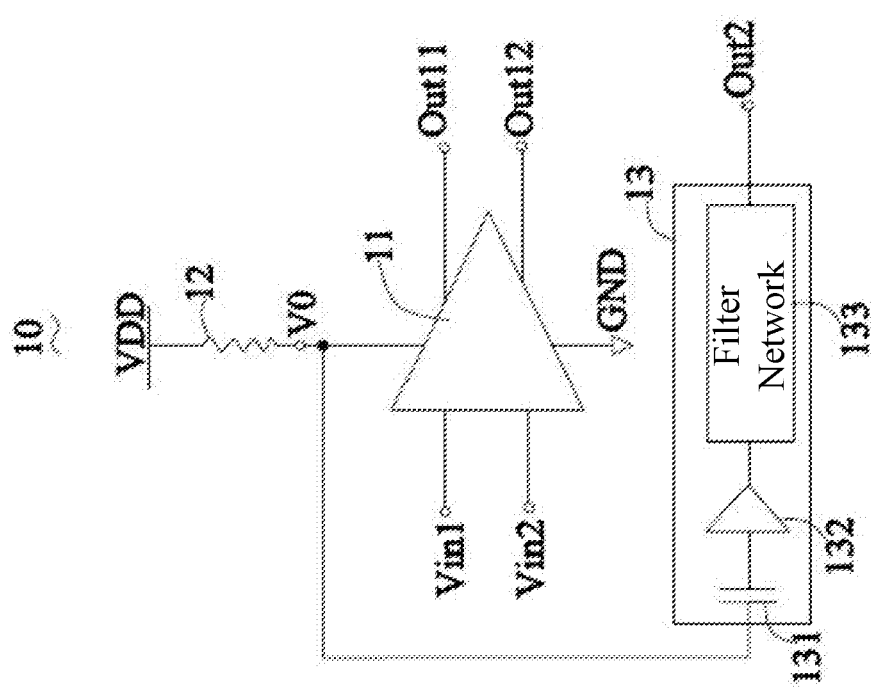
FIG. 2 is a schematic circuit diagram of a transceiver chip of the reader for medical implants as depicted in FIG. 1.

Referring to FIG. 2, the transceiver chip 10 includes a power amplifier 11, a resistor 12 and a signal processing module 13.

The power amplifier 11 is electrically connected with the impedance matching network 20 and configured to output the first communication signal with high frequency (e.g. greater than 300 MHz). Since the power amplifier 11 has nonlinear characteristics, the second communication signal transmitted back from the RFID tag 210 can be modulated into a low frequency signal (i.e. a signal with frequency close to that of a DC electrical signal) by the power amplifier 11 while the second communication signal transmitted back from the RFID tag 210 and the first communication signal output by the power amplifier 11 can be separated in signal frequency, so that interference between the first communication signal and the second communication signal can be effectively avoided without using any external circulator or any external isolator, which can effectively save space and reduce the size of the reader 100 for medical implants.

In this embodiment, the power amplifier 11 includes a first input port Vin1, a second input port Vin2, a first output port Out11, a second output port Out12, a signal output port Out2, a voltage port V0 and a ground terminal GND. The first input port Vin1 and the second input port Vin2 are configured to receive a driving voltage signal so that the power amplifier 11 is operable. The first output port Out11 and the second output port Out12 are electrically connected with the impedance matching network 20. The signal output port Out2 is electrically connected with an external electronic device (e.g. a mobile phone or a computer). The voltage port V0 is electrically connected with a reference voltage VDD through the resistor 12. The voltage port V0 is further electrically connected with the signal processing module 13. The ground terminal GND is connected to the ground.

Since the bioelectricity of a living organism may vary the impedance of the RFID tag 210, the variation of the impedance of the RFID tag 210 may vary the load of the power amplifier 11 through coupling effect so as to vary a DC current that the power amplifier 11 draws from the reference voltage VDD.

The signal processing module 13 is configured to filter interference signals from the DC current. One port of the signal processing module 13 is electrically connected with the voltage port V0 and the other port of the signal processing module 13 is electrically connected with the signal output port Out2.

Specifically, the signal processing module 13 includes a capacitor 131, a low-noise amplifier 132 and a filter network 133.

The capacitor 131 is electrically connected with the voltage port V0 and configured to filter DC signals from the voltage port V0.

The input port of the low-noise amplifier 132 is electrically connected with the capacitor 131 and the output port of the low-noise amplifier 132 is electrically connected with the filter network 133. The low-noise amplifier 132 is configured to amplify signals filtered by the capacitor 131. The filter network 133 includes low-pass filters and the low-pass filters are modulated with Miller-Rabin primality testing algorithm and configured to filter high frequency signals from the signals amplified by the low-noise amplifier 132. Signals output by the filter network 133 are transmitted to the external electronic device through the signal output port Out2.

Figure 3:
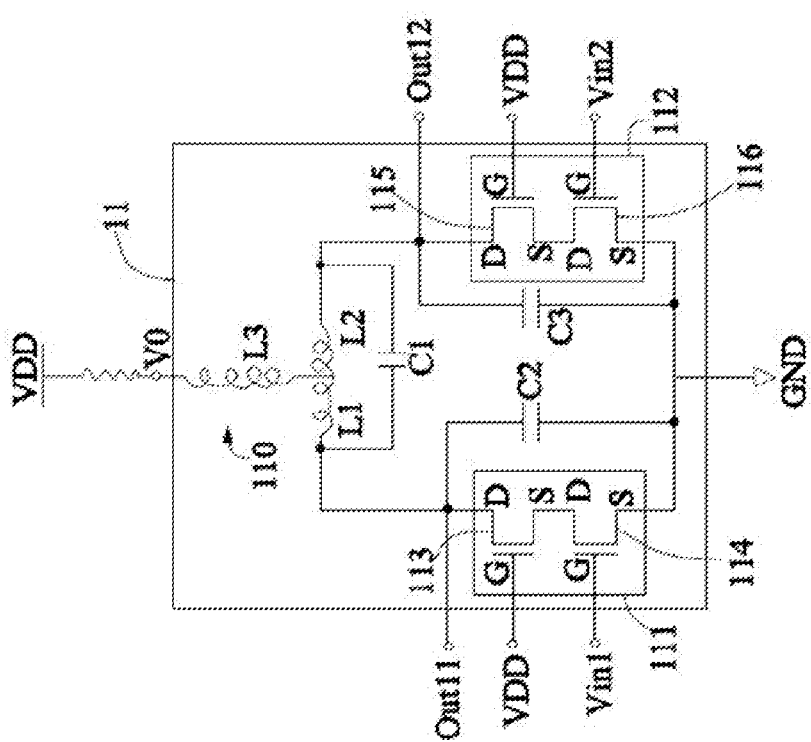
FIG. 3 is a schematic circuit diagram of a power amplifier of the transceiver chip as depicted in FIG. 2.

Referring to FIG. 3, the power amplifier 11 further includes a symmetric inductor structure 110, a first amplifying module 111, a second amplifying module 112, a first capacitor C1, a second capacitor C2 and a third capacitor C3.

The symmetric inductor structure 110 has high quality factors (i.e. Q value) and therefore can effectively reduce energy loss and save area. The impedance of the symmetric inductor structure 110 is high enough, so that most of the current flows to loads through the first output port Out11 and the second output port Out12 without being consumed by the symmetric inductor structure 110.

The symmetric inductor structure 110 includes a first inductor L1, a second inductor L2 and a third inductor L3. The first inductor L1 is electrically connected with the second inductor L2. One port of the third inductor L3 is electrically connected with the intersection of the first inductor L1 and the second inductor L2 while the other port of the third inductor L3 is electrically connected with the voltage port V0. The third inductor L3 increases the common mode inductance without varying the differential mode inductance, so that the output impedance of the third inductor L3 is relatively high in two cases of common mode and differential mode even if the area of the third inductor L3 is small.

The first amplifying module 111 is configured to increase the maximum voltage of the first output port Out11. One port of the first amplifying module 111 is electrically connected with the first output port Out11 and the port of the first inductor L1 away from the second inductor L2 while the other port of the first amplifying module 111 is connected to the ground. The first amplifying module 111 includes a first electronic switch 113 and a second electronic switch 114 which are connected in series with each other. The first electronic switch 113 and the second electronic switch 114 are N-type Metal-Oxide Semiconductor Field Effect Transistors, each including a gate electrode, a drain electrode and a source electrode. The gate electrode of the first electronic switch 113 is electrically connected with the reference voltage VDD, the drain electrode of the first electronic switch 113 being electrically connected with the first output port Out11 and the port of the first inductor L1 away from the second inductor L2, and the source electrode of the first electronic switch 113 being electrically connected with the drain electrode of the second electronic switch 114. The gate electrode of the second electronic switch 114 is electrically connected with the first input port Vin1 and the source electrode of the second electronic switch 114 is connected to the ground.

The second amplifying module 112 is configured to increase the maximum voltage of the second output port Out12. One port of the second amplifying module 112 is electrically connected with the second output port Out12 and the port of the second inductor L2 away from the first inductor L1 while the other port of the second amplifying module 112 is connected to the ground. The second amplifying module 112 includes a third electronic switch 115 and a fourth electronic switch 116 which are connected in series with each other. In this embodiment, the third electronic switch 115 and the fourth electronic switch 116 are N-type Metal-Oxide Semiconductor Field Effect Transistors, each including a gate electrode, a drain electrode and a source electrode. The gate electrode of the third electronic switch 115 is electrically connected with the reference voltage VDD, the drain electrode of the third electronic switch 115 being electrically connected with the second output port Out12 and the port of the second inductor L2 away from the first inductor L1, and the source electrode of the third electronic switch 115 being electrically connected with the drain electrode of the fourth electronic switch 116. The gate electrode of the fourth electronic switch 116 is electrically connected with the second input port Vin2 and the source electrode of the fourth electronic switch 116 is connected to the ground.

The first capacitor C1 is connected in parallel with the first inductor L1 and the second inductor L2, while the first inductor L1 and the second inductor L2 are connected in series. Specifically, one port of the first capacitor C1 is electrically connected with the port of the first inductor L1 away from the second inductor L2 while the other port of the first capacitor C1 is electrically connected with the port of the second inductor L2 away from the first inductor L1.

The second capacitor C2 is connected in parallel with the first amplifying module 111. Specifically, one port of the second capacitor C2 is electrically connected with the first output port Out11 and the other port of the second capacitor C2 is connected to the ground.

The third capacitor C3 is connected in parallel with the second amplifying module 112. Specifically, one port of the third capacitor C3 is electrically connected with the second output port Out12 and the other port of the third capacitor C3 is connected to the ground.

The first capacitor C1, the second capacitor C2 and the third capacitor C3 are coordinated with each other and configured to filter interference signals from the first communication signal and the second communication signal.

The working process of the reader 100 for medical implants is as follows: the transceiver chip 10 transmits the first communication signal which is modulated by the impedance matching network 20 and transmitted through the antenna 30; the coil 220 receives the first communication signal and transmits the first communication signal to the RFID tag 210; the RFID tag 210 is driven by the energy of the first communication signal to transmit the second communication signal which includes the variation of the parameters of the living organism; the second communication signal is transmitted through the coil 220; the antenna 30 receives the second communication signal and transmits the second communication signal to the transceiver chip 10 through the impedance matching network 20; at this time, the variation of the parameters of the living organism varies the load of the power amplifier 11 through coupling effects so as to vary the DC current that the power amplifier 11 draws from the reference voltage VDD; the power amplifier 11 reads signals of the medical implant through the variation of the DC current; the DC current is filtered by the signal processing module 13 so that interference waves are removed therefrom and then the DC current is transmitted to the external electronic device.

Compared with the conventional readers for medical implants, the reader for medical implants of the present patent application mixes signals transmitted back from the RFID tag around DC through the nonlinear characteristics of the power amplifier and separates signals transmitted back from the RFID tag and signals output by the power amplifier in frequency while avoiding utilizing any external circulator or isolator, which effectively saves space and reduces volume. In addition, the circuit of the power amplifier occupies a relatively small area and outputs relatively high power.

While the present patent application has been shown and described with particular references to a number of embodiments thereof, it should be noted that various other changes or modifications may be made without departing from the scope of the present invention.

What is claimed is:

1. A reader for medical implants configured to read signals of a medical implant, the reader for medical implants comprising:
    an impedance matching network;
    an antenna; and
    a transceiver chip; wherein:
    the transceiver chip is connected with the antenna through the impedance matching network;
    the transceiver chip is configured to produce a first communication signal with high frequency and transmit the first communication signal to the medical implant through the impedance matching network and the antenna;

the medical implant receives the first communication signal and produces a second communication signal according to variation of parameters of the medical implant;

the antenna is configured to receive the second communication signal and transmit the second communication signal to the transceiver chip through the impedance matching network;

the transceiver chip is further configured to read signals of the medical implant according to the second communication signal;

the transceiver chip is further configured to modulate the second communication signal into a low frequency signal, so that the first communication signal can be separated from the second communication signal in frequency and interference between the first communication signal and the second communication signal can be avoided;

the transceiver chip comprises a power amplifier, a resistor and a signal processing module;

the power amplifier comprises a first input port, a second input port, a first output port, a second output port, a voltage port and a signal output port;

the first input port and the second input port are configured to receive a driving voltage signal;

the power amplifier is configured to produce the first communication signal with high frequency according to the driving voltage signal and transmit the first communication signal to the impedance matching network through the first output port and the second output port;

the voltage port is electrically connected with a reference voltage through the resistor;

the power amplifier is further configured to vary a DC current which flows through the resistor according to the second communication signal and read signals of the medical implant according to variation of the DC current;

the signal processing module is configured to filter interference signals from the DC current, produce a filtered signal and transmit the filtered signal to an external electronic device through the signal output port;

the power amplifier further comprises a symmetric inductor structure, a first amplifying module and a second amplifying module;

the symmetric inductor structure is electrically connected with the voltage port;

the first amplifying module comprises a first electronic switch and a second electronic switch which are connected in series with each other;

the first electronic switch and the second electronic switch are N-type Metal-Oxide Semiconductor Field Effect Transistors, each comprising a gate electrode, a drain electrode and a source electrode;

the gate electrode of the first electronic switch is electrically connected with the reference voltage, the drain electrode of the first electronic switch being electrically connected with the symmetric inductor structure and the first output port, the source electrode of the first electronic switch being electrically connected with the drain electrode of the second electronic switch;

the gate electrode of the second electronic switch is electrically connected with the first input port and the source electrode of the second electronic switch is connected to the ground;

the structure of the second amplifying module is the same as the structure of the first amplifying module while the second amplifying module comprises a third electronic switch and a fourth electronic switch which are connected in series with each other;

the third electronic switch and the fourth electronic switch are N-type Metal-Oxide Semiconductor Field Effect Transistors, each comprising a gate electrode, a drain electrode and a source electrode;

the gate electrode of the third electronic switch is electrically connected with the reference voltage, the drain electrode of the third electronic switch being electrically connected with the symmetric inductor structure and the second output port, the source electrode of the third electronic switch being electrically connected with the drain electrode of the fourth electronic switch; and the gate electrode of the fourth electronic switch is electrically connected with the second input port and the source electrode of the fourth electronic switch is connected to the ground.

2. The reader for medical implants of claim 1, wherein the symmetric inductor structure has high quality factors and comprises a first inductor, a second inductor and a third inductor; two ports of the first inductor are electrically connected with the second inductor and the drain electrode of the first electronic switch respectively; two ports of the second inductor are electrically connected with the first inductor and the drain electrode of the third electronic switch respectively; one port of the third inductor is electrically connected with an intersection of the first inductor and the second inductor while the other port of the third inductor is electrically connected with the voltage port.

3. A reader for medical implants configured to read signals of a medical implant, the reader for medical implants comprising:

an antenna; and a transceiver chip connected with the antenna; wherein:

the transceiver chip comprises a power amplifier and a resistor;

the power amplifier is electrically connected with a reference voltage through the resistor; the power amplifier is configured to produce a first communication signal with high frequency and transmit the first communication signal to the medical implant through the antenna;

the medical implant receives the first communication signal and produces a second communication signal according to variation of parameters of the medical implant;

the power amplifier is configured to receive the second communication signal through the antenna so as to vary a DC current which flows through the resistor and read signals of the medical implant according to variation of the DC current; and the power amplifier is further configured to modulate the second communication signal into a low frequency signal, so that the first communication signal can be separated from the second communication signal in frequency and interference between the first communication signal and the second communication signal can be avoided.

4. The reader for medical implants of claim 3, wherein the power amplifier comprises a first input port, a second input port, a first output port, a second output port, a voltage port and a signal output port; the first input port and the second input port are configured to receive a driving voltage signal; the power amplifier is configured to produce the first communication signal with high frequency according to the driving voltage signal; the first output port and the second output port are configured to output the first communication signal; the voltage port is electrically connected with the reference voltage through the resistor; the power amplifier is configured to vary the DC current which flows through the resistor according to the second communication signal; the signal output port is configured to transmit the DC current to an external electronic device.

5. The reader for medical implants of claim 4, wherein the power amplifier further comprises a symmetric inductor structure, a first amplifying module and a second amplifying module; the symmetric inductor structure is electrically connected with the reference voltage through the resistor; the first amplifying module is electrically connected with the symmetric inductor structure and the first output port and configured to increase the maximum voltage of the first output port; the second amplifying module is electrically connected with the symmetric inductor structure and the second output port and configured to increase the maximum voltage of the second output port.

6. The reader for medical implants of claim 5, wherein the symmetric inductor structure has high quality factors and comprises a first inductor, a second inductor and a third inductor; the first inductor is electrically connected with the second inductor; one port of the third inductor is electrically connected with an intersection of the first inductor and the second inductor while the other port of the third inductor is electrically connected with the voltage port.

7. The reader for medical implants of claim 6, wherein the first amplifying module comprises a first electronic switch and a second electronic switch which are connected in series with each other; the first electronic switch and the second electronic switch are N-type Metal-Oxide Semiconductor Field Effect Transistors, each comprising a gate electrode, a drain electrode and a source electrode; the gate electrode of the first electronic switch is electrically connected with the reference voltage, the drain electrode of the first electronic switch being electrically connected with the first output port and a port of the first inductor away from the second inductor, the source electrode of the first electronic switch being electrically connected with the drain electrode of the second electronic switch; the gate electrode of the second electronic switch is electrically connected with the first input port while the source electrode of the second electronic switch is connected to the ground; the structure of the second amplifying module is the same as the structure of the first amplifying module while the second amplifying module comprises a third electronic switch and a fourth electronic switch which are connected in series with each other; the third electronic switch and the fourth electronic switch are N-type Metal-Oxide Semiconductor Field Effect Transistors, each comprising a gate electrode, a drain electrode and a source electrode; the gate electrode of the third electronic switch is electrically connected with the reference voltage, the drain electrode of the third electronic switch being electrically connected with the second output port and a port of the second inductor away from the first inductor, the source electrode of the third electronic switch being electrically connected with the drain electrode of the fourth electronic switch; the gate electrode of the fourth electronic switch is electrically connected with the second input port while the source electrode of the fourth electronic switch is connected to the ground.

8. The reader for medical implants of claim 7, wherein the power amplifier further comprises a first capacitor, a second capacitor and a third capacitor; the first capacitor is connected in parallel with the first inductor and the second inductor, while the first inductor and the second inductor are connected in series with each other; the second capacitor is connected in parallel with the first amplifying module; the third capacitor is connected in parallel with the second amplifying module.

9. The reader for medical implants of claim 4, wherein the transceiver chip further comprises a signal processing module configured to filter interference signals from the DC current; one port of the signal processing module is electrically connected with the voltage port while the other port of the signal processing module is electrically connected with the signal output port.

10. The reader for medical implants of claim 3 further comprising an impedance matching network, wherein the transceiver chip is electrically connected with the antenna through the impedance matching network; the impedance matching network is electrically connected with the transceiver chip and configured to optimize transmission efficiency of the first communication signal which is transmitted by the transceiver chip through impedance matching; the antenna is electrically connected with the impedance matching network and configured to transmit the first communication signal which is modulated by the impedance matching network and further configured to transmit the second communication signal to the impedance matching network; the impedance matching network is further configured to modulate the second communication signal so that receiving efficiency of the second communication signal is optimized.

11. A reader for medical implants configured to read signals of a medical implant, the reader for medical implants comprising:
an antenna, and
a transceiver chip connected with the antenna; wherein
the transceiver chip comprises a power amplifier and a resistor;
the power amplifier is electrically connected with a reference voltage through the resistor;
the power amplifier is configured to produce a first communication signal with high frequency and transmit the first communication signal to the medical implant through the antenna;
the medical implant receives the first communication signal and produces a second communication signal according to variation of parameters of the medical implant; and
the power amplifier is configured to receive the second communication signal through the antenna so as to vary a DC current which flows through the resistor and read signals of the medical implant according to variation of the DC current.

12. The reader for medical implants of claim 11, wherein the power amplifier comprises a first input port, a second input port, a first output port, a second output port, a voltage port and a signal output port; the first input port and the second input port are configured to receive a driving voltage signal; the power amplifier is configured to produce the first communication signal with high frequency according to the driving voltage signal; the first output port and the second output port are configured to output the first communication signal; the voltage port is electrically connected with the reference voltage through the resistor; the power amplifier is configured to vary the DC current which flows through the resistor according to the second communication signal; the signal output port is configured to transmit the DC current to an external electronic device.

13. The reader for medical implants of claim 12, wherein the power amplifier further comprises a symmetric inductor structure, a first amplifying module and a second amplifying module; the symmetric inductor structure is electrically connected with the reference voltage through the resistor; the first amplifying module is electrically connected with the symmetric inductor structure and the first output port and configured to increase the maximum voltage of the first output port; the second amplifying module is electrically connected with the symmetric inductor structure and the second output port and configured to increase the maximum voltage of the second output port.

14. The reader for medical implants of claim 13, wherein the symmetric inductor structure has high quality factors and comprises a first inductor, a second inductor and a third inductor; the first inductor is electrically connected with the second inductor; one port of the third inductor is electrically connected with an intersection of the first inductor and the second inductor while the other port of the third inductor is electrically connected with the voltage port.

15. The reader for medical implants of claim 14, wherein the first amplifying module comprises a first electronic switch and a second electronic switch which are connected in series with each other; the first electronic switch and the second electronic switch are N-type Metal-Oxide Semiconductor Field Effect Transistors, each comprising a gate electrode, a drain electrode and a source electrode; the gate electrode of the first electronic switch is electrically connected with the reference voltage, the drain electrode of the first electronic switch being electrically connected with the first output port and a port of the first inductor away from the second inductor, the source electrode of the first electronic switch being electrically connected with the drain electrode of the second electronic switch; the gate electrode of the second electronic switch is electrically connected with the first input port while the source electrode of the second electronic switch is connected to the ground; the structure of the second amplifying module is the same as the structure of the first amplifying module while the second amplifying module comprises a third electronic switch and a fourth electronic switch which are connected in series with each other; the third electronic switch and the fourth electronic switch are N-type Metal-Oxide Semiconductor Field Effect Transistors, each comprising a gate electrode, a drain electrode and a source electrode; the gate electrode of the third electronic switch is electrically connected with the reference voltage, the drain electrode of the third electronic switch being electrically connected with the second output port and a port of the second inductor away from the first inductor, the source electrode of the third electronic switch being electrically connected with the drain electrode of the fourth electronic switch; the gate electrode of the fourth electronic switch is electrically connected with the second input port while the source electrode of the fourth electronic switch is connected to the ground.

16. The reader for medical implants of claim 15, wherein the power amplifier further comprises a first capacitor, a second capacitor and a third capacitor; the first capacitor is connected in parallel with the first inductor and the second inductor, while the first inductor and the second inductor are connected in series with each other; the second capacitor is connected in parallel with the first amplifying module; the third capacitor is connected in parallel with the second amplifying module.

17. The reader for medical implants of claim 12, wherein the transceiver chip further comprises a signal processing module configured to filter interference signals from the DC current; one port of the signal processing module is electrically connected with the voltage port while the other port of the signal processing module is electrically connected with the signal output port.

18. The reader for medical implants of claim 11 further comprising an impedance matching network, wherein the transceiver chip is electrically connected with the antenna through the impedance matching network; the impedance matching network is electrically connected with the transceiver chip and configured to optimize transmission efficiency of the first communication signal which is transmitted by the transceiver chip through impedance matching; the antenna is electrically connected with the impedance matching network and configured to transmit the first communication signal which is modulated by the impedance matching network and further configured to transmit the second communication signal to the impedance matching network; the impedance matching network is further configured to modulate the second communication signal so that receiving efficiency of the second communication signal is optimized.

* * * * *